US006287541B1

(12) United States Patent
Creeth et al.

(10) Patent No.: US 6,287,541 B1
(45) Date of Patent: Sep. 11, 2001

(54) ORAL CARE COMPOSITIONS

(75) Inventors: Jonathan E. Creeth, Bebington; Keiran Molloy; Philip Wright, both of Bath, all of (GB)

(73) Assignee: Chesebrough-Pond's USA Co., divison of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/401,880

(22) Filed: Sep. 23, 1999

(30) Foreign Application Priority Data

Sep. 23, 1998 (EP) .................................................. 98307733

(51) Int. Cl.[7] .......................... A61K 9/16; A61K 31/555; A61K 31/28; A61K 31/295; A61K 31/30
(52) U.S. Cl. .......................... 424/49; 514/184; 514/189; 424/630; 424/642; 424/646; 424/647; 424/648; 424/650
(58) Field of Search .................... 424/49–58; 514/184

(56) References Cited

U.S. PATENT DOCUMENTS

| | | | |
|---|---|---|---|
| 3,818,107 | * | 6/1974 | Yolles ....................................... 426/3 |
| 4,018,934 | * | 4/1977 | Parliment .............................. 426/540 |
| 4,067,962 | * | 1/1978 | Juneja ...................................... 424/52 |
| 4,575,502 | * | 3/1986 | Hider et al. ........................... 514/184 |
| 4,665,064 | * | 5/1987 | Hider et al. ........................... 514/184 |
| 4,834,983 | * | 5/1989 | Hider et al. ........................... 514/184 |
| 4,861,767 | * | 8/1989 | Hider et al. ........................... 514/184 |
| 5,028,411 | * | 7/1991 | Callingham et al. ................. 514/184 |
| 5,037,634 | | 8/1991 | Williams et al. . |
| 5,104,865 | * | 4/1992 | Hider et al. ........................... 514/184 |
| 5,268,174 | * | 12/1993 | Sakuma et al. .................... 424/195.1 |
| 5,587,147 | | 12/1996 | Domke et al. . |
| 5,628,986 | * | 5/1997 | Sanker et al. ........................... 424/49 |
| 5,696,169 | * | 12/1997 | Otsu et al. ............................. 514/675 |
| 6,025,312 | * | 2/2000 | Saito et al. .............................. 510/30 |
| 6,096,328 | * | 8/2000 | Sagel et al. ........................... 424/401 |

FOREIGN PATENT DOCUMENTS

| | | |
|---|---|---|
| 1 507 846 | 4/1978 | (GB) . |
| 2035084 * | 6/1980 | (GB) . |
| 61109716 * | 5/1986 | (JP) . |
| 04041418 * | 2/1992 | (JP) . |
| 11021222 * | 12/1999 | (JP) . |
| 11343220 * | 12/1999 | (JP) . |
| 95 13057 * | 5/1995 | (WO) . |
| 20000 16736 * | 3/2000 | (WO) . |

* cited by examiner

Primary Examiner—Shep K. Rose
(74) Attorney, Agent, or Firm—Milton L. Honig

(57) ABSTRACT

The invention relates to an oral care composition with antiplaque agents. The antiplaque agents are complexes of divalent copper, zinc, iron or tin, or trivalent iron with a specific class of cyclic α-hydroxyketones. A typical example is the copper (II)-ethylmaltol complex. These complexes are more active antiplaque agents that e.g. copper-hinokitiol complexes.

11 Claims, No Drawings

ORAL CARE COMPOSITIONS

BACKGROUND OF THE INVENTION

1. The present invention relates to oral care compositions comprising particular antiplaque agents. More particularly, it relates to oral care compositions comprising certain copper, zinc, iron or tin metal complexes comprising biologically active ligands as antiplaque agents.

2. The Related Art

It is already known, that copper and zinc metals complexes comprising certain biologically active ligands have an antimicrobial activity. Thus, for example, in EP-A-0728478 (Otsuka Pharmaceutical Co., Ltd.), copper-hinokitiol and zinc-hinokitiol complexes are described, which are stated to have antimicrobial activity. According to this publication, these copper- and zinc-hinokitiol complexes can be usefully included in oral care compositions.

Hinokitiol is a 4-isopropyl tropolone, a cyclic α-hydroxyketone having the structure

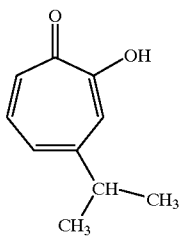

SUMMARY OF THE INVENTION

We have now found that a different class of cyclic α-hydroxyketones are biologically active ligands, capable of forming complexes with copper, zinc, iron and tin, said complexes having an antiplaque activity which is superior to the aforementioned copper- and zinc-hinokitiol complexes.

The class of cyclic α-hydroxyketones according to the present invention is represented by the following general structural formula:

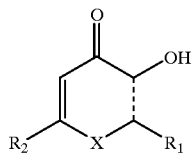

in which X represents O or $NR_3$, $R_1$ and $R_3$ represent H or a $C_1$–$C_{16}$, preferably a $C_1$–$C_4$ branched or straight-chain alkylgroup, and $R_2$ represents H or a hydroxymethylgroup. The link between the carbon atoms in the ring structure at positions 2 and 3 can be saturated or unsaturated, and is preferably unsaturated.

This class of cyclix α-hydroxyketones embraces, therefore, derivatives of hydroxypyran-4-ones and hydroxypyridin-4-ones. Typical examples of these cyclic α-hydroxyketones are maltol (=3-hydroxy-2-methyl-4H-pyran-4-one), X being 0, $R_1$ being methyl and $R_2$ being H; ethylmaltol (3-hydroxy-2-ethyl-4H-pyran-4-one), X being O, $R_1$ being ethyl and $R_2$ being H; kojic acid (5-hydroxy-2-(hydroxymethyl)-4H-pyran-4-one), X being O, $R_1$ being H and $R_2$ being hydroxymethyl; 2-methyl-3-hydroxypyridin-4-one, X=$NR_1$, $R_3$=H, $R_1$=methyl and $R_2$=H; 1,2-dimethyl-3-hydroxypyridin-4-one, X=$NR_3$, $R_3$=methyl, R1=methyl and R2=H; and 1-ethyl-2-methyl-3-hydroxypyridin-4-one, X=$NR_3$,$R_3$=ethyl, $R_1$=methyl and $R_2$=H.

The metals which are complexed by the above class of cyclic α-hydroxyketones are divalent copper, zinc, iron and tin and trivalent iron.

DETAILED DESCRIPTION OF THE INVENTION

The cyclic α-hydroxyketones of the present invention, and the metal complexes thereof, are known in the art and can be synthesised by established methodologies, as e.g. described in Acta Cryst. B32 (1976) page 3121 by Berg, et al., in Can. J. Chem. 68, (1990) page 1598 by Annan, et al., J. Chem. Soc., Dalton Trans. (1992) page 2375 by Denekamp, et al., in J. Med. Chem. 37 (1994 page 461 by El-Jammal, et al., and in J. Med. Chem. 39 (1996) page 3659 by Ellis, et al.. Suitable complexes can be formed from a suitable divalent copper, zinc, iron or stannous salt or a trivalent iron salt with the cyclic α-hydroxyketones in molar ratios of between 10:1 to 1:10, preferably 4:1 to 1:4, particularly preferably 2:1 to 1:2 (the molar ratio being calculated on the basis of the metal ion).

The preferred metal complexes according to the present invention are the $Cu^{2-}$ and $Sn^{2-}$ complexes, particularly the $Cu^{2+}$- and $Sn^{2:}$ malton and -ethylmalton complexes.

The metal complexes of the present invention are included in the oral care compositions in an amount, ranging from 0.001 to 5% by weight of the composition, preferably 0.1 to 3% by weight, and optimum results are obtained with amounts, ranging from 0.2 to 2 by weight of the composition. Mixtures of the various metal complexes may also be used. The complexes may be prepared prior to their incorporation in the oral care composition, or they may be prepared in situ during the manufacture of the oral care composition. It may sometimes be advantageous to use an amount of the cyclic α-hydroxyketone, in excess of the stochiometric equivalent, required for the formation of the complex, to prevent possible decomposition of the complexes in the oral care composition during storage, and to possibly further increase the antiplaque activity of the complexes. It has also been found that it is sometimes advantageous to use an excess of the metal salt, e.g. the copper or stannous salt, to further increase the antiplaque activity.

The oral care compositions of the present invention may furthermore comprise optional, conventional ingredients such as pharmaceutically acceptable carriers like starch, sucrose, water or water/alcohol systems etc.. Small amounts of surfacants may also be included, such as anionic, nonionic, cationic and zwitterionic or amphoteric surfacants. They may comprise particulate abrasive materials such as silicas, aluminas, calcium carbonates, dicalciumphosphates, calcium pyrophosphates, hydroxyapatites, trimetaphosphates, insoluble hexametaphosphates and so on, including agglomerated particulate abrasive materials, usually in amounts between 3 and 60% by weight. In the case of the calcium carbonates being used as the abrasive materials, the metal complexes of the present invention are more compatible with such materials than other metal salts, e.g. copper salts, which are according to EP-B-38867 (Blendax) rather incompatible with calcium carbonates.

Furthermore, they may comprise humectants such as glycerol, sorbitol, propyleneglycol, xylitol, lactitol and so on.

Binders and thickeners such as sodium carboxymethylcellulose, xanthan gum, gum arabic etc. may also be included, as well as synthetic polymers such as polyacrylates and carboxyvinyl polymers such as Carbopol®.

Flavours such as peppermint and spearmint oils may also be included, as well as preservatives, opacifying agents, colouring agents, pH-adjusting agents, sweetening agents and so on.

Additional anti-bacterial agents may also be included such as Triclosan, chlorohexidine, copper-, zinc- and stannous salts such as zinc citrate, sodium zinc citrate and stannous pyrophosphate, sanguinarine extract, metronidazole. Further examples of anti-bacterial agents are quaternary ammonium compounds such as cetylpyridinium chloride; bis-guanides such as chlorhexidine digluconate, hexetidine, octenidine, alexidine; halogenated bisphenolic compounds such as 2,2' methylenebis-(4-chloro-6-bromophenol).

Polymeric compounds which can enhance the delivery of active ingredients such as anti-bacterial agents can also be included. Examples of such polymers are copolymers of polyvinylmethylether with maleic anhydride and other similar delivery enhancing polymers, e.g. those described in DE-A-3,942,643 (Colgate)

While the complexes of the present invention are particularly useful as anti-plaque agents, they are also useful as antimicrobial- and anti-gingivitis agents in oral care products.

Furthermore anti-inflammatory agents such as ibuprofen, flurbiprofen, aspirin, indomethacin etc. may also be included.

Anti-caries agents such as sodium- and stannous fluoride, aminefluorides, sodium monofluorophosphate, casein, plaque buffers such as urea, calcium lactate, calcium glycerophosphate, strontium polyacrylates may also be included. Other optional ingredients include vitamins such as Vitamin C, and plant extracts. Desensitizing agents such as glycerolmonooleate potassium citrate, potassium chloride, potassium tartrate, potassium bicarbonate, potassium oxalate, potassium nitrate as well as strontium salts may also be included.

Buffers and salts to buffer the pH and ionic strength of the compositions may also be included. Liposomes and other encapsulates may also be used to improve delivery or stability of active ingredients.

Furthermore, the oral compositions may comprise anti-calculus agents such as alkalimetal pyrophosphates, hypophosphite-containing polymers, organic phosphonates, phosphocitrates etc..

In addition, the compositions may comprise functional biomolecules such as bacteriocins, antibodies, enzymes and Other optional ingredients that may be included are e.g. bleaching agents such as peroxy compounds e.g. potassium peroxydiphosphate, effervescing systems such as sodium bicarbonate/citric acid systems, colour change systems, and so on.

The toothpastes may also be formulated into systems for use in dual-compartment type dispensers.

The present invention will be further illustrated by way of Example.

EXAMPLE 1

In vitro biofilm antiplaque tests were carried out with copper salts, and copper complexes of hinokitiol and maltol.

The test is based on monitoring the growth (by measuring absorbance) of a biofilm of a single species of bacteria, formed in the wells of a 96 well plate, after treatment with toothpaste slurries, and calculating the time taken to reach a chosen turbidity (i.e. a chosen absorbance value at 630 nm;

A sample of S. warneri was cultured overnight in BHI medium. The culture was centrifuged and washed twice with phosphate-buffered saline (PBS) to an approximate optical density of 1.0. A 200 µl aliquot of bacterial suspension was pipetted into wells of a maleic anhydride-activated polystyrene 96-well plate (Pierce-Warriner, Chester). Plates were covered with a sterile plate sealer (to prevent contamination), centrifuged (3000 rpm, 4 minutes) and incubated for 1 hour at 37° C. Plates were used on the day of preparation, and were kept until use at room temperature, or if not required for several hours, at 4° C. Biofilm-coated wells were washed three times with PBS taking care to avoid disrupting the bacteria.

Toothpaste slurries were prepared by mixing paste with water to give 33% (w/w) slurries and centrifuging for 10 or 20 minutes at 3,500 rpm (Heraeus Labofuge 400 or MSE Mistral 1000 centrifuge). The supernatant was decanted into sterile containers and used within a day.

After washing plates, wells were treated with 200 µl of toothpaste supernatant for 30 seconds. Plates were inverted over a beaker of Virkon sterilizing solution, dried by patting down on absorbent paper, washed three times with sterile Milli-Q grade and dried by patting down on absorbent paper.

After treatment and washing, 200 µl of BHI followed by 80 µl of sterile light mineral oil was added to each well. Plates were incubated at 37° C. in a microtitre plate reader (Dynes Technologies DIAS) and growth monitored at 630 nm every 15 minutes for 16 hours. The end-point was taken as the time taken to reach an $A_{630}$ of 0.4. This absorbance approximated to the inflection point of the growth curve for each bacterium, where growth of the culture is most rapid. The point of maximum growth rate was taken as it is the least sensitive to variations in the background absorbance and the most sharply resolved point on the time axis. The time to reach the optical density of 0.4 was recorded. The longer the growth time, the more effective the treatment.

In a conventional toothpaste containing chalk as the abrasive cleaning agent, the following results were obtained:

| Time to reach the optical density (O.D.) of 0.4 (in hrs) | % by weight of Cu (as CuSO4) | % by weight of maltol |
|---|---|---|
| 5.32 | — | — |
| 5.39 | 0.1 | — |
| 5.14 | — | 0.1 |
| 12.29 | 0.1 | 0.1 |
| 4.15 | — | 0.2 |
| 10.26 | 0.1 | 0.2 |

These results show, that the copper (II)-maltol complex (formed in situ as evidenced by the formation of a green colour in the paste) has a significantly greater antibacterial effect than either CuSO4 or maltol alone, as evidenced by the significantly longer periods to reach the O.D. of 0.4

Repeating these tests with a conventional toothpaste containing silica as the abrasive agent gave the following results:

| Time to reach the (O.D.) of 0.4 (in hrs) | % by weight of Cu (as CuSO4) | % by weight of maltol |
|---|---|---|
| 4.88 | — | — |
| 6.20 | 0.1 | — |
| 5.10 | — | 0.1 |
| 13.86 | 0.1 | 0.1 |
| 4.79 | — | 0.2 |
| 12.92 | 0.1 | 0.2 |

These results also clearly show the superiority of the copper (II)-maltol complex over coppersulphate as antibacterial agent.

Repeating these experiments in a model toothpaste solution gave the following results

| Time to reach the optical density (O.D.) of 0.4 (in hrs) | % by weight of Cu (as CuSO4) | % by weight of maltol |
|---|---|---|
| 4.34 | — | — |
| 6.49 | 0.1 | — |
| 4.38 | — | 0.1 |
| 9.39 | 0.1 | 0.1 |
| 4.69 | — | 0.2 |
| 9.57 | 0.1 | 0.2 |

For comparison, 0.25% of CuSO4 and 0.25% hinokitiol produced a growth time to reach the O.D. of 0.4 of 7 hrs, 0.25% CuSO4 alone 4.82 hrs, 0.25% hinokitiol alone 4.54 hrs.

Increasing the amounts of maltol, at a level of CuSO4 of 0.1%, gave the following results in the above model toothpaste solution test

| Time to (O.D.) of 0.4 (in hrs) | % by weight of maltol |
|---|---|
| 4.03 | — |
| 9.66 | 0.1 |
| 9.72 | 0.2 |
| 9.38 | 0.5 |
| 8.55 | 1 |

In all the above tests, the copper (II) sulphate was its pentahydrate salt.

Similar results are obtained when using the zinc, iron and stannous complexes of maltol and ethylmaltol.

Example 2

The following toothpastes were prepared:

| PRODUCT INGREDIENT | 1. (PLACEBO) | 2. | 3. | 4. |
|---|---|---|---|---|
| SORBITOL (70%) | 45.00 | 45.00 | 45.00 | 45.00 |
| SODIUM SACCHARIN | 0.17 | 0.17 | 0.17 | 0.17 |
| TITANIUM DIOXIDE | 1.00 | 1.00 | 1.00 | 1.00 |
| POLYETHYLENE | 5.00 | 5.00 | 5.00 | 5.00 |

-continued

| PRODUCT INGREDIENT | 1. (PLACEBO) | 2. | 3. | 4. |
|---|---|---|---|---|
| GLYCOL 1500 | | | | |
| THICKENING SILICA | 8.00 | 8.00 | 8.00 | 8.00 |
| ABRASIVE SILICA | 10.00 | 10.00 | 10.00 | 10.00 |
| CELLULOSE GUM | 0.90 | 0.90 | 0.90 | 0.90 |
| SODIUM LAURYL SULPHATE | 1.50 | 1.50 | 1.50 | 1.50 |
| FLAVOUR | 1.00 | 1.00 | 1.00 | 1.00 |
| COPPER SULPHATE PENTAHYDRATE | — | 0.20 | 0.20 | 0.20 |
| HINOKITIOL | — | — | 0.20 | — |
| ETHYLMALTOL | — | — | — | 0.20 |
| ETHANOL | — | — | — | 1.0 |
| WATER | TO 100% | TO 100% | TO 100% | TO 100% |

The plaque inhibition (PGI) by these products was measured according to the plaque growth inhibition test method as described by Harrap in J. Clin. Periodontol (1) (1974) pp. 166–174, using single brushing and product 1 as placebo, and measuring the plaque at the beginning of the test and after 18 hours. The PGI is expressed as a percentage according to the formula:

$$PGI\ (\%) = \left\{1 - \frac{PG_{18\,hrs(test)} - PG_{0\,hrs(test)}}{PG_{18\,hrs(placebo)} - PG_{0\,hrs(placebo)}}\right\} \times 100$$

| Product | PGI (%) | Std. Error | p |
|---|---|---|---|
| 2 | 15.16 | 11.43 | n.s. |
| 3 | 11.98 | 12.45 | n.s. |
| 4 | 26.31 | 10.686 | 0.026 |

These results show, that the copper (II) ethylmaltol complex has a significantly higher PGI than the placebo, whereas the PGI of copper alone or the copper-hinokitiol complex was not significantly different from the placebo.

What is claimed is:

1. An oral care composition comprising from about 0.001 to about 5% by weight of an antiplaque agent, which is a complex of a metal selected from the group consisting of copper, zinc, iron and tin metal ions complexed to a biologically active ligand which is a cyclic α-hydroxyketone of the following general formula:

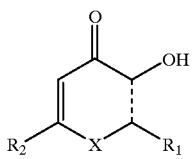

in which X represents O, $R_1$ represents H or a $C_1$–$C_{16}$ branched or straight-chain alkylgroup, and $R_2$ represents H, linkage between carbon atoms at ring positions 2 and 3 being saturated or unsaturated.

2. An oral care composition according to claim 1, wherein the linkage is unsaturated.

3. An oral care composition according to claim 1, wherein $R_1$ represents H or a $C_1$–$C_4$ branched or straight-chain alkyl group.

4. An oral care composition according to claim 1, wherein the complex is a divalent copper complex.

5. An oral care composition according to claim 1 characterised in that the cyclic α-hydroxyketone is ethylmaltol.

6. An oral care composition according to claim 1 wherein the complex is a divalent tin complex.

7. An oral care composition according to claim 1, wherein the cyclic α-hydroxyketone is maltol.

8. An oral care composition according to claim 1 wherein the complex is a divalent copper ethylmaltol complex.

9. A method of inhibiting microbial growth in an oral cavity by applying to the oral cavity an oral care composition comprising from about 0.001 to about 5% by weight of an antiplaque agent, which is a complex of a metal selected from the group consisting of copper, zinc, iron and tin metal ions complexed to a biologically active ligand which is a cyclic α-hydroxyketone of the following general formula:

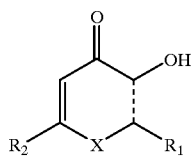

in which X represents O, $R_1$ represents H or a $C_1$–$C_{16}$ branched or straight-chain alkylgroup, and $R_2$ represents H, linkage between carbon atoms at ring positions 2 and 3 being saturated or unsaturated.

10. A method for inhibiting plaque in an oral cavity comprising applying to the oral cavity an oral care composition comprising from about 0.001 to about 5% by weight of an antiplaque agent, which is a complex of a metal selected from the group consisting of copper, zinc, iron and tin metal ions complexed to a biologically active ligand which is a cyclic α-hydroxyketone of the following general formula:

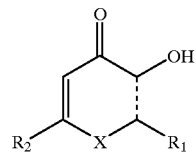

in which X represents O, $R_1$ represents H or a $C_1$–$C_{16}$ branched or straight-chain alkylgroup, and $R_2$ represents H, linkage between carbon atoms at ring positions 2 and 3 being saturated or unsaturated.

11. A method for inhibiting gingivitis in an oral cavity comprising applying to the oral cavity an oral care composition comprising from about 0.001 to about 5% by weight of an antiplaque agent, which is a complex of a metal selected from the group consisting of copper, zinc, iron and tin metal ions complexed to a biologically active ligand which is a cyclic α-hydroxyketone of the following general formula:

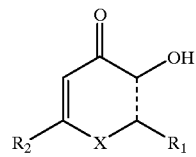

in which X represents O, $R_1$ represents H or a $C_1$–$C_{16}$ branched or straight-chain alkylgroup, and $R_2$ represents H, linkage between carbon atoms at ring positions 2 and 3 being saturated or unsaturated.

* * * * *